US012757903B2

(12) United States Patent
Chen et al.

(10) Patent No.: US 12,757,903 B2
(45) Date of Patent: Oct. 13, 2026

(54) BIOLOGICAL SEED-COATING AGENT (SCA) INCLUDING FERMENTATION BROTH OBTAINED BASED ON CO-CULTIVATION OF TRICHODERMA AND BACILLUS SEQUENTIALLY INOCULATED, AND PREPARATION METHOD THEREOF

(71) Applicant: SHANGHAI JIAO TONG UNIVERSITY, Shanghai (CN)

(72) Inventors: Jie Chen, Shanghai (CN); Peng Liu, Shanghai (CN); Xinhua Wang, Shanghai (CN)

(73) Assignee: SHANGHAI JIAO TONG UNIVERSITY, Shanghai (CN)

( * ) Notice: Subject to any disclaimer, the term of this patent is extended or adjusted under 35 U.S.C. 154(b) by 502 days.

(21) Appl. No.: 18/260,041

(22) PCT Filed: Jun. 22, 2022

(86) PCT No.: PCT/CN2022/100273

§ 371 (c)(1),
(2) Date: Jun. 30, 2023

(87) PCT Pub. No.: WO2022/268093

PCT Pub. Date: Dec. 29, 2022

(65) Prior Publication Data

US 2024/0057615 A1 Feb. 22, 2024

(30) Foreign Application Priority Data

Jun. 23, 2021 (CN) ......................... 202110700561.2

(51) Int. Cl.

| | |
|---|---|
| ***A01N 63/38*** | (2020.01) |
| ***A01N 43/22*** | (2006.01) |
| ***A01N 43/38*** | (2006.01) |
| ***A01N 61/02*** | (2006.01) |
| ***A01N 63/22*** | (2020.01) |
| ***A01N 63/50*** | (2020.01) |
| ***C12N 1/145*** | (2026.01) |
| ***C12N 1/205*** | (2026.01) |
| ***C12N 3/00*** | (2006.01) |
| *C12R 1/125* | (2006.01) |
| *C12R 1/885* | (2006.01) |

(52) U.S. Cl.

CPC ............. *A01N 63/38* (2020.01); *A01N 43/22* (2013.01); *A01N 43/38* (2013.01); *A01N 61/02* (2013.01); *A01N 63/22* (2020.01); *A01N 63/50* (2020.01); *C12N 1/145* (2021.05); *C12N 1/205* (2021.05); *C12N 3/00* (2013.01); *C12R 2001/125* (2021.05); *C12R 2001/885* (2021.05)

(58) Field of Classification Search

CPC ........ A01N 63/38; A01N 63/22; C12N 1/145; C12N 1/205; C12N 1/14; C12N 1/20; C12R 2001/125; C12R 2001/885

See application file for complete search history.

(56) References Cited

U.S. PATENT DOCUMENTS

| | | | | |
|---|---|---|---|---|
| 6,808,917 B1 * | 10/2004 | Johnson | .................. A01C 1/06 435/252.4 |
| 2016/0058016 A1 | 3/2016 | Villegas Escobar et al. | |
| 2016/0278384 A1 | 9/2016 | Jabs et al. | |

FOREIGN PATENT DOCUMENTS

| | | | | |
|---|---|---|---|---|
| CN | 101358176 A | 2/2009 | |
| CN | 104904751 A | 9/2015 | |
| CN | 109536411 A | 3/2019 | |
| CN | 110938562 A | 3/2020 | |
| CN | 111631231 * | 9/2020 | ............. A01N 43/12 |
| CN | 113444649 A | 9/2021 | |
| WO | 2019155252 A1 | 8/2019 | |

OTHER PUBLICATIONS

Translation of CN111631231 by Google Patents, 8 pages, 2020 (Year: 2020).*

Liu, Huazhen, et al., Studies on Enzyme Inhibitor Produced by Microorganism: I. Methods of Screening for Proteases Inhibitors, Chinese Journal of Antibiotics, 1983, pp. 275-279, vol. 8 No.5.

Valliappan Karuppiah, et al., Simultaneous and sequential based co-fermentations of Trichoderma asperellum GDFS1009 and Bacillus amyloliquefaciens 1841: a strategy to enhance the gene expression and metabolites to improve the bio-control and plant growth promoting activity, Microbial Cell Factories, 2019, pp. 1-16, vol. 18 No. 185.

Qiong Wu, et al., Co-culture of Bacillus amyloliquefaciens ACCC11060 and Trichoderma asperellum GDFS1009 enhanced pathogen-inhibition and amino acid yield, Microbial Cell Factories, 2018, pp. 1-12, vol. 17 No. 155.

Valliappan Karuppiah, et al., Co-cultivation of Trichoderma asperellum GDFS1009 and Bacillus amyloliquefaciens 1841 Causes Differential Gene Expression and Improvement in the Wheat Growth and Biocontrol Activity, Frontiers in Microbiology, 2019, pp. 1-16, vol. 10, Article 1068.

Chen, Zenan, et al., Research Progress on Preventing Plant Diseases and Insect Pests of Seed Coating Formulation, J. Anhui Agric. Sci., 2018, pp. 10-13, vol. 46 No. 32.

Chen Jie, Advances on Trichoderma-induced Plant Resistance against Diseases, Chinese Journal of Biological Control, 2015, pp. 733-741, vol. 31 No.5.

(Continued)

*Primary Examiner* — Thane Underdahl

(74) *Attorney, Agent, or Firm* — Bayramoglu Law Offices LLC

(57) ABSTRACT

A biological seed-coating agent (SCA) including a fermentation broth obtained based on co-cultivation of *Trichoderma* and *Bacillus* sequentially inoculated, and a preparation method thereof are provided. According to a principle of synthesis biology, *Trichoderma* that induces disease resistance and stress resistance and *Bacillus* that antagonizes pathogens and promotes crop growth are inoculated in stages for co-fermentation to prepare a microbial co-culture solution. The microbial co-culture solution is mixed with diatomaceous earth and brassinolide according to a specified ratio to prepare a biological SCA in a dosage form of a powder. The biological SCA includes high contents of spores and antagonistic and growth-promoting substances.

2 Claims, 2 Drawing Sheets

(56) References Cited

OTHER PUBLICATIONS

S. Chandra Nayaka, et al., Seed biopriming with a novel strain of Trichoderma harzianum for the control of toxigenic Fusarium verticillioides and fumonisins in maize, Archives of Phytopathology and Plant Protection, 2010, pp. 264-282, vol. 43 No. 3.

* cited by examiner

BIOLOGICAL SEED-COATING AGENT (SCA) INCLUDING FERMENTATION BROTH OBTAINED BASED ON CO-CULTIVATION OF TRICHODERMA AND BACILLUS SEQUENTIALLY INOCULATED, AND PREPARATION METHOD THEREOF

CROSS REFERENCE TO THE RELATED APPLICATIONS

This application is the national phase entry of International Application No. PCT/CN2022/100273, filed on Jun. 22, 2022, which is based upon and claims priority to Chinese Patent Application No. 202110700561.2, filed on Jun. 23, 2021, the entire contents of which are incorporated herein by reference.

TECHNICAL FIELD

The present disclosure relates to a technique for preparing a biological seed-coating agent (SCA) based on co-cultivation (co-fermentation) of *Trichoderma* and *Bacillus* and a use of the biological SCA. Specifically, a microbial co-culture solution is prepared mainly through co-fermentation, and then a biological SCA in a dosage form of a powder is prepared with diatomaceous earth to adsorb the microbial co-culture solution and brassinolide as an additive. This biological SCA has high contents of *Trichoderma* and *Bacillus* live spores, antimicrobial peptaibols, indoleacetic acid (IAA), or the like, and thus exhibits characteristics such as a strong ability to induce disease resistance of a crop and a strong ability to promote the growth of a crop.

BACKGROUND

Chemical SCAs are agrochemical agents most commonly used in current food crop production in China to control soil-borne diseases and underground pests, promote the growth of crops, and improve stress resistance. With the implementation of the "pesticide and fertilizer double reduction" plan in agricultural production in China, SCAs need to be eco-friendly and ecological. It has been proved by practice that microbial SCAs are an important way to provide seed probiotics. Microbial SCAs can reduce the harm of traditional agrochemicals to soil, and can also improve a microbial community structure in soil for a crop and promote the growth of a crop. However, the current microbial SCAs mainly have problems such as single effective microbial strains, poor spore stress resistance and activity, insufficient microbial metabolite utilization and unstable performance of plant disease prevention and crop growth-promoting effects. Therefore, the development and utilization of a multi-microbes SCA is of great significance for the improvement of the quality and efficacy of a biological SCA.

As one of the internationally-recognized biocontrol fungi, *Trichoderma* exhibits excellent prevention and restoration effects for soil-borne diseases and agricultural soil pollution. *Trichoderma* can produce biological disease control-associated substances such as hydrophobic proteins, chitinases, dextranases, proteases, and antagonistic secondary metabolites (Chen Jie, Progress of Research on Induction of *Trichoderma* for Disease Resistance of Plants [J], Chinese Journal of Biological Control, 2014, 31 (5): 733-741), and a single-*Trichoderma* biological SCA has been developed internationally (Nayaka S. C, et al. Seed biopriming with a novel strain of *Trichoderma harzianum* for the control of toxigenic *Fusarium verticillioides* and fumonisins in maize, Archiv für Pflanzenschutz. 2010, 264-282), which is mainly used in corn production. As one of the internationally-recognized biocontrol bacteria, *Bacillus* is mainly used for biological control of leaf diseases and growth promotion and can secrete antagonistic substances such as proteins, lipopeptides, and secondary metabolites thereof and growth-promoting substances such as IAA and indolebutyric acid (IBA). Currently, microbial agents of *Trichoderma* or *Bacillus* alone are commonly used in the control of crop diseases and promotion of crop growth but gradually exhibit shortcomings in use. For example, a microbial agent of *Trichoderma* alone shows an obvious control effect for soil-borne diseases, but has poor stress resistance; and a microbial agent of *Bacillus* alone has an obvious control effect for leaf diseases and strong stress resistance, but exhibits a weaker ability to induce crop resistance against disease and environmental adverse factors than *Trichoderma*. Therefore, in many manufacturers inside and outside China, *Trichoderma* and *Bacillus* are separately used to conduct fermentation, and then resulting fermentation broths are mixed to prepare a composite preparation, but it still cannot fully solve the problem of product homogeneity with *Trichoderma* and *Bacillus* inside and outside China. With the development of synthetic biology, the *Trichoderma/Bacillus* co-fermentation technology has become a research hotspot. *Trichoderma* and *Bacillus* interact with each other during a co-fermentation process to induce the production of a series of novel primary and secondary metabolites which is usually lacked in single culture of either one, those novel metabolites provide a material basis for the preparation of novel biological SCAs. Therefore, the research on a technique for preparing a novel biological SCA based on co-fermentation with *Trichoderma* and *Bacillus* is of great significance for the improvement of an innovation level of biological SCAs in China.

SUMMARY

An objective of the present disclosure is to provide a method for preparing a biological SCA based on co-cultivation of *Trichoderma* and *Bacillus*, and a use method of the biological SCA. A technical focus of the present disclosure is as follows: A screened *Trichoderma* and *Bacillus* affinity combination is used to conduct co-fermentation by an established sequential inoculation method to obtain a fermentation broth with high contents of *Trichoderma* and *Bacillus* spores, antimicrobial peptaibols (such as alamethicin), and growth-regulating substances (such as IAA), and then a two-microbes co-culture SCA is prepared through adsorption of diatomaceous earth, thereby improving effects of the biological SCA to promote crop growth and control diseases.

The present disclosure is implemented by the following technical solutions:

1. A method for preparing a biological SCA based on co-cultivation of *Trichoderma* and *Bacillus* is provided, including the following steps:

S1: preparing a fermentation broth obtained based on co-cultivation of *Trichoderma* and *Bacillus;*

S2: mixing the fermentation broth obtained based on co-cultivation of *Trichoderma* and *Bacillus* with diatomaceous earth and brassinolide; and S3: detecting a quality of the biological SCA in a dosage form of a powder.

2. In S1, a co-fermentation technique is used to increase an interaction metabolism level of *Trichoderma* and *Bacillus* while maintaining comparable numbers of spore of the two types of microbes.

As a preferred embodiment, in S1, a preparation method of the fermentation broth includes:

inoculating *Trichoderma* into a potato dextrose agar (PDA) medium, cultivating at 28° C. for 5 d, punching with a 5 mm puncher, inoculating a resulting *Trichoderma* disc into a potato dextrose (PD) medium, and cultivating in the PD medium for 3 d; transfer a resulting *Trichoderma* seed culture into a co-culture medium in a fermentation tank, and conducting fermentation at 28° C. for 48 h, with a ventilation of 0.8 vvm to 1 vvm, a pH of 5.0 to 5.6, and a rotational speed of 120 rpm;

inoculating the *Bacillus* into a lysogeny broth agar (LBA) medium, cultivating at 30° C. for 2 d, punching with a 5 mm puncher, inoculating a resulting *Bacillus* disc into a lysogeny broth (LB) medium, and cultivating at 30° C. for 2 d; and inoculating a resulting *Bacillus* seed culture into a *Trichoderma* fermentation broth (co-culture medium) obtained after 2 d of fermentation, and conducting co-fermentation with a ventilation of 1 vvm to 1.3 vvm, a pH adjusted by ammonia water to 4.5 to 5.5, and a rotational speed of 140 rpm. During fermentation, according to a co-fermentation time range of 45 h to 50 h, when a *Bacillus* spore formation rate is 85%, a *Trichoderma* chlamydospore formation rate is 90%, an antimicrobial peptaibol alamethicin content reaches 0.1 μg/L to 0.5 μg/L, and an IAA content reaches 2,000 μg/L to 2,500 μg/L, fermentation is completed, and a resulting fermentation broth is discharged.

As a preferred embodiment, in S2, the fermentation broth obtained based on co-cultivation of *Trichoderma* and *Bacillus*, diatomaceous earth, and brassinolide are mixed and dried as follows:

after the co-fermentation is completed, separating enriched mixed spores through solid-liquid separation (SLS) by a centrifuge, thoroughly mixing the enriched mixed spores, diatomaceous earth, and 0.1% brassinolide according to a mass ratio of 25%:60%:15%, oven-drying a resulting mixture in a spore dryer (at 45° C. to 48° C.) until a moisture content is 5%, and sieving a resulting dried material through an 80-mesh sieve to obtain a *Trichoderma-Bacillus*-brassinolide dry-powder biological SCA.

As a preferred embodiment, in S3, a dilution-plate method is used to detect the microbial co-culture powder, and detection results are as follows: *Trichoderma* spore content: $0.8\times10^8$ cfu/g to $1.5\times10^8$ cfu/g, *Bacillus* spore content: $2.0\times10^9$ cfu/g to $5.0\times10^9$ cfu/g, antimicrobial peptaibol (alamethicin) content: 0.1039 μg/L, and IAA content: 2159.53 μg/L.

DETAILED DESCRIPTION OF THE EMBODIMENTS

Figure 1:
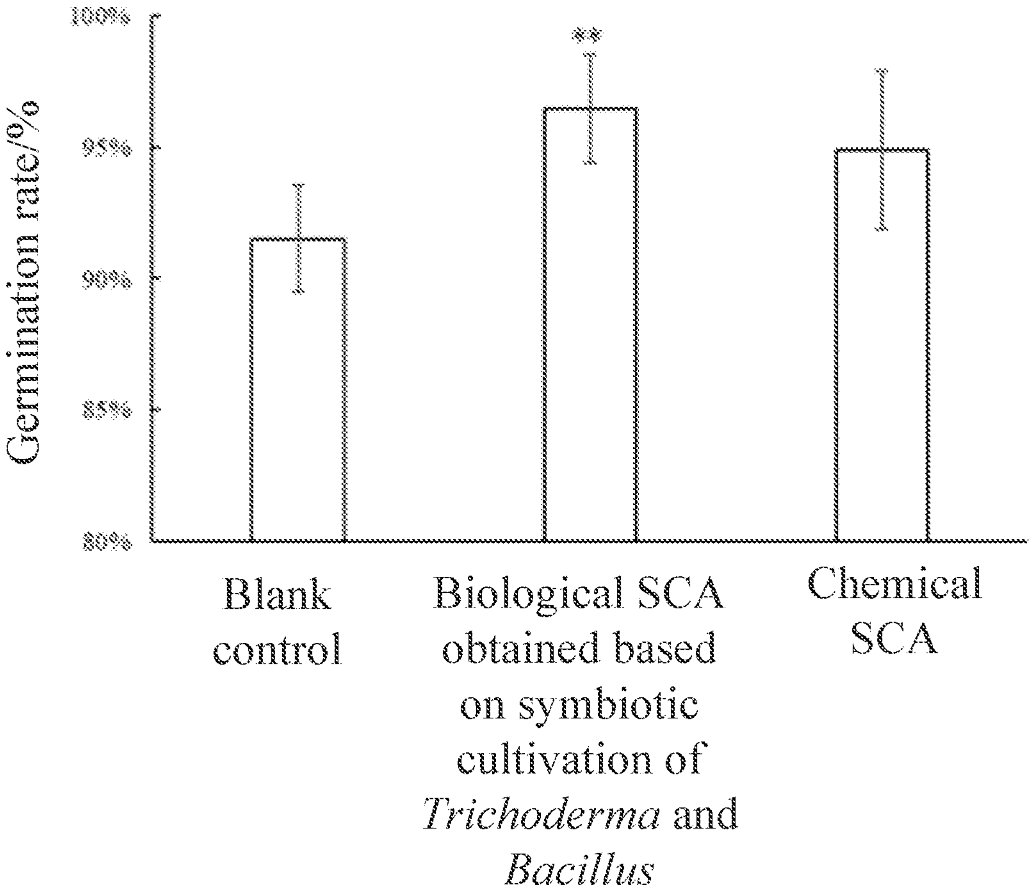
FIG. 1 shows the influence of SCAs on a wheat emergence rate.

The present disclosure is described in detail below with reference to specific examples. The following examples will help those skilled in the art to further understand the present disclosure, but do not limit the present disclosure in any way. It should be noted that those of ordinary skill in the art can further make several variations and improvements without departing from the idea of the present disclosure. These all fall within the protection scope of the present disclosure.

Example 1

A biological SCA obtained based on co-fermentation of *Trichoderma* and *Bacillus* was prepared, and specific steps were as follows:

1. Plate cultivation of *Trichoderma* and *Bacillus: Trichoderma* was inoculated into a PDA medium and cultivated at 28° C. for 3 d. *Bacillus* was inoculated into an LBA medium and cultivated at 30° C. for 2 d.

PDA medium: 200 g of a potato was taken, peeled, diced, and then steamed; a resulting supernatant was taken, 20 g of glucose and 20 g of an agar powder were added, and a resulting mixture was diluted with deionized water to 1 L, dispensed into 250 mL erlenmeyer flasks, and autoclaved at 121° C. for 30 min.

PD medium: 200 g of a potato was taken, peeled, diced, and then steamed; a resulting supernatant was taken, 20 g of glucose was added, and a resulting mixture was diluted with deionized water to 1 L, dispensed into 250 mL erlenmeyer flasks, and autoclaved at 121° C. for 30 min.

LBA medium: 5 g of a yeast extract, 10 g of sodium chloride, 10 g of tryptone, and 20 g of an agar powder were mixed, a resulting mixture was diluted with deionized water to 1 L and dispensed into 250 mL erlenmeyer flasks, a pH was adjusted with NaOH to 7.0, and a resulting medium was autoclaved at 121° C. for 20 min.

LB medium: 5 g of a yeast extract, 10 g of sodium chloride, and 10 g of tryptone were mixed, a resulting mixture was diluted with deionized water to 1 L and dispensed into 250 mL erlenmeyer flasks, a pH was adjusted with NaOH to 7.0, and a resulting medium was autoclaved at 121° C. for 20 min.

2. Preparation of a *Trichoderma-Bacillus* co-fermentation medium: 20 g/L corn flour, 20 g/L yeast extract powder, and 20 g/L molasses were mixed, and a pH of a resulting medium was adjusted with sodium hydroxide to 6.0 to 6.5.

3. Control of a sequential inoculation and co-fermentation process: In a 300 L fermentation tank, a fermentation medium was sterilized at 121° C. for 30 min; after the sterilization was completed, a *Trichoderma* seed culture was inoculated into a co-culture medium (1% v/v), and fermentation was conducted for 40 h with a ventilation of 1 vvm, a rotational speed of 180 rpm, a temperature of 28° C., and a pH adjusted by ammonia water to 4.5 to 5.5, a *Bacillus* seed culture was inoculated into a resulting fermentation broth (2.0% v/v), and co-fermentation was conducted for 48 h; and when a *Bacillus* spore formation rate reached 85% and a *Trichoderma* chlamydospore formation rate reached 90%, a resulting fermentation broth was discharged.

4. Detection of a quality of the co-fermentation: Contents of IAA and alamethicin in each of a *Trichoderma-Bacillus* co-fermentation supernatant and a *Trichoderma* fermentation supernatant were detected. In the co-fermentation supernatant, an alamethicin content was 0.1039 μg/L and an IAA content was 2159.53 μg/L, which were significantly higher than those in a supernatant obtained after fermentation of *Trichoderma* alone and a supernatant obtained after fermentation of *Bacillus* alone; and contents of the antimicrobial peptaibol (alamethicin) and IAA in a co-fermentation broth were significantly higher than those in a single-strain fermentation broth (as shown in Table 1).

5. Preparation of a dry-powder SCA based on co-cultivation of *Trichoderma* and *Bacillus* After the co-fermentation was completed, enriched mixed spores were separated through SLS by a centrifuge, the enriched mixed spores, diatomaceous earth, and 0.1% brassinolide were thoroughly mixed according to a mass ratio of 3:6:1, oven-dried in a spore dryer (at 45° C.) until a moisture content was 5%, and sieved through an 80-mesh sieve to obtain a *Trichoderma-Bacillus*-brassinolide dry-powder biological SCA.

TABLE 1

Analysis of contents of alamethicin and IAA in a supernatant obtained after co-fermentation of *Trichoderma* and *Bacillus* and a supernatant obtained after fermentation of *Trichoderma* alone

| Fermentation type | Component type | Component content, μg/L |
|---|---|---|
| Co-fermentation of *Trichoderma* and *Bacillus* | IAA | 2159.53 |
| | Alamethicin | 0.1039 |
| Fermentation of *Trichoderma* alone | IAA | 23.82 |
| | Alamethicin | 0.0865 |
| Fermentation of *Bacillus* alone | IAA | 620.45 |
| | Alamethicin | 0.0120 |

Example 2

A growth-promoting effect of the biological SCA obtained based on co-cultivation of *Trichoderma* and *Bacillus* was detected in the field.

Test site: Henan Academy of Agricultural Sciences, Zhumadian

Test steps:

1. Preparation of field experimental materials

Variety: Jimai 22

Biological SCA: A dry-powder SCA obtained based on co-cultivation of *Trichoderma* and *Bacillus*

Chemical SCAs: 90% thiamethoxam, 8.5% tebuconazole, and a 1.5% film-forming agent (control)

2. The chemical SCAs (agent-to-seed ratio: 1:200) and the dry-powder SCA obtained based on co-cultivation of *Trichoderma* and *Bacillus* (agent-to-seed ratio: 1:100) each was used for seed dressing.
3. 20 d after the seeds were sown, the influence of each treatment on wheat emergence was investigated.
4. There was a very significant difference in emergence rate between the biological SCA and the blank control; and the influence of the biological SCA on a wheat emergence rate was similar to or better than the influence of the chemical SCAs on a wheat emergence rate (as shown in FIG. 1, it should be noted that data in FIG. 1 were an average of 5 replicates and a standard error thereof. **: one-way analysis of variance (ANOVA) indicated a very significant difference, 0.01<P<0.001).

Example 3

A control effect of the dry-powder SCA obtained based on co-cultivation of *Trichoderma* and *Bacillus* for soil-borne diseases of corn was verified in the field.

Test site. A farm of Shenyang Agricultural University

Test steps:

1. Field experimental materials:
2. Variety: Zhengdan 958
3. Biological SCA: A dry-powder SCA obtained based on co-cultivation of *Trichoderma* and *Bacillus*, which was used with an agent-to-seed ratio of 1:100.
4. Chemical SCAs: 90% thiamethoxam, 8.5% tebuconazole, and a 1.5% film-forming agent, which each was used with an agent-to-seed ratio of 1:200.
5. Sowing mode: Dibbling, 4,000 plants/mu.
6. Pathogen inoculation: When sowing, *Fusarium graminearum* (*F graminearum*) and *Rhizoctonia solani* (*R. solani*) each was inoculated into the soil at an inoculum size of 5%, in mid-to-late July, a lower leaf sheath was inoculated by the wheat grain-cultured *R solani*; and in early August, a fruit ear was inoculated with *Fusarium verticilloides* (*F. verticilloides*) by a toothpick method.

Control Effect Investigation and Production Test.

1. At a milk ripening stage, 5 diagonal points were investigated for each treatment, 4 rows were randomly selected for each point, and 50 plants were randomly investigated for each row. A disease incidence (including a lodging rate) of each treatment was investigated, and a field control effect of stalk rot was statistically analyzed.

2. At a milk ripening stage, 5 diagonal points were investigated for each treatment, 4 rows were randomly selected for each point, and 50 plants were randomly investigated for each row. A disease incidence and a disease level per plant for each treatment were investigated, and a disease index and a field control effect for corn sheath blight were statistically analyzed.

Disease indexes of corn sheath blight were shown in Table 2.

TABLE 2

Grading criteria for corn sheath blight

| Disease rank | Symptom description |
|---|---|
| 1 | The 4th leaf sheath under a fruit ear and lower leaf sheaths are diseased. |
| 3 | The 3rd leaf sheath under a fruit ear and lower leaf sheaths are diseased. |
| 5 | The 2nd leaf sheath under a fruit ear and lower leaf sheaths are diseased. |
| 7 | The 1st leaf sheath under a fruit ear and lower leaf sheaths are diseased |
| 9 | A fruit ear and upper leaf sheaths are diseased. |

3. At a milk ripening stage, 4 rows of each treatment were randomly selected, and 10 ears were randomly selected from each row. Bracts were peeled off, a disease level of each ear was investigated and recorded, and a disease index and a control effect for the ear were statistically analyzed. Grading criteria for disease incidence of corn ears were shown in Table 3.

TABLE 3

Grading criteria for corn ear rot

| Disease rank | Symptom description |
|---|---|
| 1 | A diseased area is 0% to 1% of a total area of a fruit ear. |
| 3 | A diseased area is 2% to 10% of a total area of a fruit ear. |
| 5 | A diseased area is 11% to 25% of a total area of a fruit ear. |
| 7 | A diseased area is 26% to 50% of a total area of a fruit ear. |
| 9 | A diseased area is 51% to 100% of a total area of a fruit ear. |

4. Yield Measurement Method

At a harvest stage, 5 points were selected for each treatment to investigate 10 $m^2$ of plants. 10 to 20 plants were selected from each point and investigated, and a number of corn ears, a thousand-grain weight, and a moisture content in grains at harvest each was measured. A yield of each plot was recorded, a yield per acre was calculated, and a yield increase rate in contrast to a blank control (in the blank control, neither the dry-powder SCA obtained based on co-cultivation of *Trichoderma* and *Bacillus* or the chemical SCA was added) was calculated.

5. Field test results showed that the dry-powder SCA obtained based on co-cultivation of *Trichoderma* and *Bacillus* could effectively reduce the occurrence of stalk rot and significantly increase the yield (as shown in Table 4).

TABLE 4

Corn stalk rot control effect and yield increase effect of the dry-powder SCA obtained based on co-cultivation of *Trichoderma* and *Bacillus*

| Treatment | Incidence (%) | Control effect (%) | Number of ears/10 $m^2$ | Thousand-grain weight/g | Yield kg/mu | Yield increase rate (%) |
|---|---|---|---|---|---|---|
| Dry-powder SCA obtained based on co-cultivation of *Trichoderma* and *Bacillus* | 0.93 ± 0.46a | 74.86 | 53.67a | 372.80 ± 15.55a | 736.80 ± 9.72a | 19.28 |
| Chemical SCA | 1.39 ± 0.80a | 62.43 | 54.33a | 350.10 ± 31.65a | 712.95 ± 3.11a | 15.42 |
| Blank control | 3.70 ± 0.46b | — | 53.33a | 317.10 ± 31.65a | 617.70 ± 9.95b | — |

The dry-powder SCA obtained based on co-cultivation of *Trichoderma* and *Bacillus* exhibited an excellent control effect for corn sheath blight and an excellent yield increase effect (as shown in Table 5 and Table 6).

TABLE 5

Corn sheath blight control effect and yield increase effect of the dry-powder SCA obtained based on co-cultivation of *Trichoderma* and *Bacillus* (plot 1)

| Treatment | Disease index | Control effect (%) | Number of ears/10 $m^2$ | Thousand-grain weight/g | Yield kg/mu | Yield increase rate (%) |
|---|---|---|---|---|---|---|
| Dry-powder SCA obtained based on co-cultivation of *Trichoderma* and *Bacillus* | 33.81 ± 5.67ab | 48.80 | 59.33a | 352.67 ± 7.68a | 746.50 ± 11.33a | 10.31 |
| Chemical SCA | 42.01 ± 1.60b | 36.38 | 58.33a | 349.23 ± 19.83a | 720.15 ± 3.11a | 6.43 |
| Blank control | 66.03 ± 3.06c | — | 56.33a | 317.03 ± 16.78a | 676.73 ± 10.51a | — |

The SCA obtained based on co-cultivation of *Trichodermna* and *Bacillus* could improve the ear rot control effect and yield increase rate (Table 6).

TABLE 6

Corn sheath blight control effect and yield increase effect of the dry-powder SCA obtained based on co-cultivation of *Trichoderma* and *Bacillus* (plot 2)

| Treatment | Disease index | Control effect (%) | Number of ears/10 $m^2$ | Thousand-grain weight/g | Yield KG/667 $m^2$ | Yield increase rate (%) |
|---|---|---|---|---|---|---|
| Dry-powder SCA obtained based on co-cultivation of | 23.81 ± 0.58a | 36.86 | 59.37a | 363.67 ± 9.14a | 757.94 ± 9.40a | 16.93 |

TABLE 6-continued

Corn sheath blight control effect and yield increase effect of the dry-powder SCA obtained based on co-cultivation of *Trichoderma* and *Bacillus* (plot 2)

| Treatment | Disease index | Control effect (%) | Number of ears/10 $m^2$ | Thousand-grain weight/g | Yield KG/667 $m^2$ | Yield increase rate (%) |
|---|---|---|---|---|---|---|
| *Trichoderma* and *Bacillus* Chemical SCA | 26.06 ± 1.65a | 30.89 | 57.67a | 352.67 ± 14.50a | 726.67 ± 8.39a | 12.10 |
| Blank control | 37.71 ± 0.58b | — | 57.67a | 328.83 ± 8.20a | 648.21 ± 7.67b | — |

Example 4

Control Effects of SCAs Obtained Based on Co-Cultivation of *Trichoderma* and *Bacillus* for FHB 1. Test site: A farm of Shanghai Jiao Tong University (Minhang Campus)

Test materials: *Bacillus subtilis* (*B. subtilis*) BS-22, *Trichoderma aureoviride* (*T. aureoviride*) SG3403, *F. graminearum*, *Rhizoctonia solani*, and wheat variety Ningmai 13.

2. Preparation of dry-powder and liquid SCAs: A microbial co-culture solution, a film-forming agent, and water were mixed in a ratio of 8:1:1 to obtain a liquid SCA. A microbial co-culture solution and talcum powder were mixed in a ratio of 1:5 (ml:g) and then oven-dried in a 40° C. oven for 5 h to 6 h to obtain a dry-powder SCA.

3. *F. graminearum* was cultivated in a shaking flask for about 7 d ($2\times10^8$ cfu/L).

4. Pot soil was prepared with an organic seedling medium and vermiculite in a ratio of 3:1 (V/V). The prepared pot soil was filled into flower pots (high×diameter: 27 cm×23 cm). Then coated wheat seeds (Ningmai 13) were sown, with 10 seeds per pot and a covered soil thickness of 1 cm.

5. 14 d to 21 d after sowing, three wheat plants were randomly selected from each pot and then tested for the plant height and fresh weight. At a wheat flowering stage, an *F graminearum* spore suspension inoculum was diluted 50-fold ($1\times10^7$ cfu/L) and then sprayed onto wheat plants, and the wheat plants were highly moisturized with a humidifier. 20 d later, the incidence of FHB was observed, and the disease index and control effect were investigated. FIG. 1 shows the influence of treatment of different SCAs on a wheat emergence rate.

Figure 2:
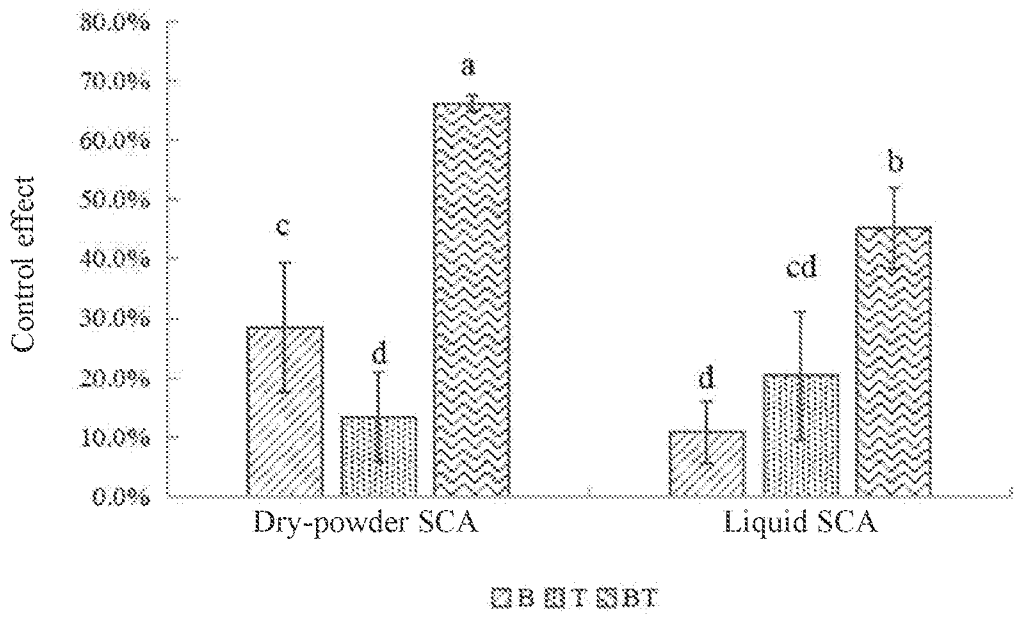
FIG. 2 shows the control effects of SCAs obtained based on co-cultivation of *Trichoderma* and *Bacillus* for *Fusarium* head blight (FHB).

6. FIG. 2 shows the control effects of SCAs obtained based on co-cultivation of *Trichoderma* and *Bacillus* for FHB. It can be seen from FIG. 2 that control effects of treatments with a microbial agent obtained after fermentation of *Bacillus* alone, a microbial agent obtained after fermentation of *Trichoderma* alone, and the dry-powder SCA obtained after co-fermentation of *Trichoderma* and *Bacillus* reach 28.4%, 13.4%, and 66.2%, respectively (namely, the bars d, cd, and b for the dry-powder SCA in the figure), indicating that a control effect of the treatment with the dry-powder SCA for FHB is significantly higher than that of other treatments; and control effects of treatments with a microbial agent obtained after fermentation of *Bacillus* alone, a microbial agent obtained after fermentation of *Trichoderma* alone, and the liquid SCA obtained after co-fermentation of *Trichoderma* and *Bacillus* reach 10.9%, 20.4%, and 45.2%, respectively (namely, the bars c, d, and a for the liquid SCA in the figure), indicating that a control effect of the treatment with the liquid SCA for FHB is significantly higher than that of other treatments.

It should be noted that B in FIG. 2 represents a microbial agent obtained after fermentation of *Bacillus* alone; T represents a microbial agent obtained after fermentation of *Trichoderma* alone; and BT represents an SCA obtained after co-fermentation of *Trichoderma* and *Bacillus*. For significance differences of the above control effects: P<0.05.

Compared with the prior art, one or more embodiments of the present disclosure have the following beneficial effects.

1. A fermentation broth obtained after co-fermentation of *Trichoderma* and *Bacillus* has higher contents of alamethicin and IAA than a fermentation broth obtained after fermentation of *Trichoderma* alone. It should be noted that, unlike the co-cultivation used in the prior art, co-fermentation is adopted in the present disclosure, which can overcome an antagonism or competition effect between microorganisms during co-cultivation to cause growth of a specified microorganism.

2. The dry-powder SCA obtained based on co-cultivation of *Trichoderma* and *Bacillus* has a more stable spore content than the liquid SCA.

3. The dry-powder SCA obtained based on co-cultivation of *Trichoderma* and *Bacillus* has more excellent functions of controlling diseases and promoting crop growth than a microbial agent obtained based on fermentation of *Trichoderma* or *Bacillus* alone and a simple combination of microbial agents obtained based on separate fermentation of the two.

The present disclosure is not limited to the above specific implementations, and a person skilled in the art can make various variations or modifications within the scope of the claims without affecting the essence of the present disclosure.

The specific examples of the present disclosure are described above. It should be understood that the present disclosure is not limited to the above specific implementations, and a person skilled in the art can make various variations or modifications within the scope of the claims without affecting the essence of the present disclosure. The examples of the present disclosure and features in the examples may be arbitrarily combined with each other in a non-conflicting situation.

What is claimed is:

1. A biological seed-coating agent (SCA) in a dosage form of a dry powder, comprising enriched mixed spores, a diatomaceous earth, and brassinolide, wherein the enriched mixed spores are obtained by co-cultivation of *Trichoderma* and *Bacillus* sequentially inoculated and comprise antimicrobial alamethicin and indoleacetic acid (IAA); and wherein the enriched mixed spores, diatomaceous earth, and a 0.1% brassinolide solution are mixed according to a mass ratio of 3:6:1, oven-dried in a spore dryer until a moisture content is 5%, and sieved through an 80-mesh sieve.

2. The biological SCA according to claim 1, wherein in the enriched mixed Spores obtained by the co-cultivation of the *Trichoderma* and the *Bacillus*, are prepared by steps comprising:

first inoculating the *Trichoderma* at an amount 1% v/v to 2% v/v of a total fermentation amount and cultivating at 25° C. to 28° C. for 35 h to 45 h;

inoculating the *Bacillus* at an amount 2.0% v/v to 3.0% v/v of the total fermentation amount and co-cultivating for 48 h at 28° C. to 30° C.; and separating enriched mixed spores through solid-liquid separation (SLS) by a centrifuge, wherein a content of a resulting *Trichoderma* chlamydospore is $1.0\times10^8$ cfu/g to $2.0\times10^8$ cfu/g, a content of a resulting *Bacillus* spore is $3.0\times10^9$ cfu/g to $5.0\times10^9$ cfu/g, a content of the antimicrobial alamethicin is 0.1 μg/g to 0.5 μg/g, and a content of the IAA is 2,000 μg/g to 2,500 μg/g.

* * * * *